United States Patent
Morioka et al.

(10) Patent No.: US 7,651,628 B2
(45) Date of Patent: Jan. 26, 2010

(54) COMPRESSION MOLDED PRODUCT OF EFFERVESCENT CHLORINATED ISOCYANURIC ACID

(75) Inventors: Shigeru Morioka, Itano-gun (JP); Yoshiya Iwasaki, Itano-gun (JP); Yasufumi Seo, Itano-gun (JP)

(73) Assignee: Shikoku Chemicals Corporation, Kagawa (JP)

( * ) Notice: Subject to any disclaimer, the term of this patent is extended or adjusted under 35 U.S.C. 154(b) by 515 days.

(21) Appl. No.: 10/911,496

(22) Filed: Aug. 5, 2004

(65) Prior Publication Data

US 2005/0031684 A1  Feb. 10, 2005

(30) Foreign Application Priority Data

Aug. 6, 2003  (JP)  ............... P. 2003-287668

(51) Int. Cl.
*C11D 3/395* (2006.01)
(52) U.S. Cl. .............. 252/187.34; 252/186.2
(58) Field of Classification Search .......... 252/186.2, 252/186.21, 187.34
See application file for complete search history.

(56) References Cited

U.S. PATENT DOCUMENTS

| | | | |
|---|---|---|---|
| 3,446,893 A | * | 5/1969 | Hanford et al. ............ 424/76.3 |
| 3,719,599 A | * | 3/1973 | Crivellaro et al. ............ 508/173 |
| 4,149,988 A | * | 4/1979 | Brennan et al. ......... 252/186.35 |
| 5,021,186 A | * | 6/1991 | Ota et al. ................ 252/186.35 |
| 5,486,304 A | * | 1/1996 | Eoga et al. .................. 510/102 |
| 5,958,458 A | * | 9/1999 | Norling et al. .............. 424/490 |
| 6,300,302 B1 | * | 10/2001 | Brooker et al. .............. 510/445 |
| 6,355,607 B1 | * | 3/2002 | Rahman et al. ............. 510/446 |
| 6,692,769 B1 | * | 2/2004 | Ishibashi et al. ............ 424/490 |
| 6,733,781 B2 | * | 5/2004 | Abu-Izza et al. ............ 424/464 |
| 6,992,055 B1 | * | 1/2006 | Nitta et al. .................. 510/444 |
| 2002/0061831 A1 | * | 5/2002 | Kaziska et al. ............. 510/446 |
| 2005/0250667 A1 | * | 11/2005 | Quellet et al. ............... 510/444 |

FOREIGN PATENT DOCUMENTS

| | | |
|---|---|---|
| JP | 61-192800 A | 8/1986 |
| JP | 1-139511 A | 6/1989 |

OTHER PUBLICATIONS

Particle Size-Sieve Mesh Conversion Chart accessed from: http://www.sigmaaldrich.com/Area_of_Interest/Research_Essentials/Chemicals/Key_Resources/Technical_Library/Particle_Size_Conversion.html on Oct. 7, 2008.*

* cited by examiner

*Primary Examiner*—Mark Eashoo
*Assistant Examiner*—Peter F Godenschwager
(74) *Attorney, Agent, or Firm*—Sughrue Mion, PLLC

(57) ABSTRACT

A compression molded product of effervescent chlorinated isocyanuric acid, comprising (a) chlorinated isocyanuric acid, (b) organic acid, (c) carbonate salt and (d) sodium sulfate.

4 Claims, No Drawings

COMPRESSION MOLDED PRODUCT OF EFFERVESCENT CHLORINATED ISOCYANURIC ACID

FIELD OF THE INVENTION

The present invention relates to a effervescent chlorinated isocyanuric acid molded product obtainable by press-molding a blend comprising a chlorinated isocyanuric acid, an organic acid, a carbonate salt and a sodium sulfate.

BACKGROUND ART

A chlorinated isocyanuric acid forming hypochlorous acid in an aqueous solution is known as a chlorine-based oxidizing agent and has been used in various applications due to the excellent bactericidal, bleaching, and deodorizing effects. The chlorinated isocyanuric acid is used in the form of powder or granule and, in addition, is frequently used after press-molding into tablets in view of easy handling.

Incidentally, since a compression molded product of the chlorinated isocyanuric acid exhibit a decreased dissolving rate as compared with powdery one when brought into contact with water, it has been widely conducted that a chlorinated isocyanuric acid is blended with an organic acid and a carbonate salt as a effervescent agent and the blend is formed into a molded product. For example, a reference (e.g. JP-A-61-192800) proposes a effervescent cleaning agent obtained by blending a chlorinated isocyanuric acid, adipic acid, and sodium bicarbonate or sodium carbonate and subjecting the blend to tablet formation.

However, such effervescent chlorinated isocyanuric acid molded products are sensitive to moisture in the air and hence the greatest care should be taken for the storage. That is, when a molded product comprising a chlorinated isocyanuric acid, an organic acid, and a carbonate salt is left at a place open to the outside air, it absorbs moisture in the outside air and the chlorinated isocyanuric acid, organic acid, and carbonate salt react with one another and decompose to generate chlorine-based gases and carbon dioxide gas. As a result, there arise problems that the effective chlorine content in the above molded product diminishes and also its bubbling ability decreases.

In order to prevent occurrence of the problems, the effervescent chlorinated isocyanuric acid molded products are packed under tight sealing with an aluminum-deposited film or an aluminum foil-laminated film, but there is a risk of expansion or burst of the packing bug in the case that it is stored under high temperature and humidity for a long period of time, so that a effervescent molded product excellent in storage stability has been desired.

On the other hand, a reference (e.g. JP-A-1-139511) discloses a chlorinated isocyanuric acid molded product having a good blend stability obtained by mixing a chlorinated isocyanuric acid compound or its alkali salt having a size capable of passing through 60-mesh sieve (note: sieve opening of 250 μm) with sodium sulfate having a size capable of passing through 35-mesh sieve (note: sieve opening of 420 μm) and compressing the mixture, followed by crushing and screening.

However, there is no description on the stabilizing effect of the chlorinated isocyanuric acid molded product containing a chlorinated isocyanuric acid, an organic acid, and a carbonate salt.

Moreover, at the production of a chlorinated isocyanuric acid molded product comprising sodium sulfate, crystals of sodium sulfate show a high hardness, so that there is a risk of abrading or damaging the surfaces of mortar and pestle to be used as a mold at press-molding. For solving such a problem, it is suitable to blend a lubricant such as magnesium stearate, calcium stearate, or a fatty acid ester.

However, when the chlorinated isocyanuric acid molded product containing the above lubricant is dissolved in water, the lubricant may remain undissolved in the molded-product dissolved water to give an unpleasant impression, so that it is difficult to use the lubricant for bathwater, pool-water, and the like. In addition, a fatty acid ester-based lubricant has a problem that a chlorinated isocyanuric acid is decomposed to generate chlorine-based gases by the contact of the lubricant with the chlorinated isocyanuric acid.

SUMMARY OF THE INVENTION

An object of the invention is to provide a effervescent chlorinated isocyanuric acid molded product having characteristics that abrasion of mortar and pestle to be used as a mold at press-molding can be reduced, the surface of the mortar and pestle can be hardly damaged, and the use of a lubricant can be suppressed, together with an excellent storage stability.

As a result of extensive studies for solving the above problems, the present inventors have found that a effervescent chlorinated isocyanuric acid molded product having an excellent storage stability is obtainable by press-molding a blend comprising a chlorinated isocyanuric acid, an organic acid, a carbonate salt, and sodium sulfate, and hence they have accomplished the invention.

In other words, the invention has the following constitution.

(1) A compression molded product of effervescent chlorinated isocyanuric acid, comprising:
  (a) chlorinated isocyanuric acid,
  (b) organic acid,
  (c) carbonate salt, and
  (d) sodium sulfate.

(2) The compression molded product according to the above (1), wherein
  the component (a) is contained in an amount of from 100 parts by weight,
  the component (b) is contained in an amount of from 50 to 200 parts by weight,
  the component (c) is contained in an amount of from 50 to 200 parts by weight, and
  the component (d) is contained in an amount of from 10 to 100 parts by weight.

(3) The compression molding product according to the above (1), wherein the component (d) has a particle diameter of from 45 μm to less than 355 μm.

(4) A process for producing the compression molded product according to the above (1), which comprises molding under compression a composition comprising:
  (a) chlorinated isocyanuric acid,
  (b) organic acid,
  (c) carbonate salt, and
  (d) sodium sulfate.

Moreover, by making the particle diameter of sodium sulfate from 45 μm to less than 355 μm, abrasion of mortar and pestle to be used as a mold at press-molding can be reduced, the surface of the mortar and pestle can be hardly damaged, and the use of a lubricant can be suppressed. Furthermore, the storage stability of the above molded product can be made more excellent.

The compression molded product of effervescent chlorinated isocyanuric acid of the invention has characteristics that abrasion of mortar and pestle to be used as a mold at press-molding can be reduced, the surface of the mortar and pestle can be hardly damaged, and the use of a lubricant can be suppressed, together with an excellent storage stability.

Accordingly, the molded product can be used as a bactericidal cleaning agent for water with which the human body may come into contact, such as pool-water or bathwater.

DETAILED DESCRIPTION OF THE INVENTION

The invention will be described below in detail.

(a) Chlorinated Isocyanuric Acid

The chlorinated isocyanuric acid compound for use in the invention includes trichloroisocyanuric acid, dichloroisocyanuric acid, sodium dichloroisocyanurate and its monohydrate and dihydrate, potassium dichloroisocyanurate, and the like.

Trichloroisocyanuric acid and dichloroisocyanuric acid have a property of low solubility in water and sodium dichloroisocyanurate and its monohydrate and dihydrate and potassium dichloroisocyanurate have a property of high solubility in water. Therefore, in the case that the compression molded product of effervescent chlorinated isocyanuric acid of the invention is gradually dissolved, trichloroisocyanuric acid and dichloroisocyanuric acid are suitable and in the case that the molded product is to be dissolved promptly, sodium dichloroisocyanurate and its monohydrate and dihydrate, and potassium dichloroisocyanurate are suitably used.

(b) Organic Acid

The organic acid for use in the invention includes solid acid of citric acid, tartaric acid, ascorbic acid, malic acid, fumaric acid, succinic acid, malonic acid, adipic acid, oxalic acid, lactic acid, and the like.

(c) Carbonate Salt

The carbonate salt for use in the invention includes sodium carbonate, sodium bicarbonate, potassium carbonate, potassium bicarbonate, ammonium carbonate, sodium sesquicarbonate, sodium percarbonate, and the like. Of these, sodium carbonate and sodium bicarbonate are preferred in view of the low material cost.

These organic acids and carbonate salts may be used solely or in combination of two or more of them individually.

Moreover, the blending ratios of the organic acid and the carbonate salt each independently is preferably from 50 to 200 parts by weight based on 100 parts by weight of the chlorinated isocyanuric acid. Furthermore, the blending ratio of the organic acid to the carbonate salt is preferably 1:1 as an equivalent ratio of acid to alkali.

The above organic acid and carbonate salt act as a effervescent agent and, in the case that the molded product comprising the chlorinated isocyanuric acid, the organic acid, and the carbonate salt is put into water, the organic acid reacts with the carbonate salt to generate carbon dioxide gas, so that the molded product is disintegrated with bubbling and hence the dissolution rate of the molded product can be enhanced.

(d) Sodium Sulfate

Sodium sulfate for use in the invention may have water of crystallization but it is preferred to use an anhydrous salt capable of acting also as a desiccating agent.

Moreover, the particle diameter of sodium sulfate is not particularly limited. However, sodium sulfate having a particle diameter of from 45 μm to less than 355 μm is preferred.

When the particle diameter of sodium sulfate is 45 μm or more, it is preferable because air release at molding is easy and so-called capping does not tend to occur. Furthermore, when the particle diameter is less than 355 μm, it is preferable because extrusion pressure to the molded product at removing the molded product is not high and hence abrasion of mortar and pestle used at molding is not accelerated and the surfaces of the mortar and pestle are not easily damaged. In addition, an improving effect of storage stability of the effervescent chlorinated isocyanuric acid molded product of the invention becomes excellent.

The blending ratio of sodium sulfate is preferably from 10 to 100 parts by weight based on 100 parts by weight of the chlorinated isocyanuric acid. When the ratio is 10 parts by weight or more, it is preferable because a desired storage stability can be obtained. On the other hand, when the ratio is 100 parts by weight or less, it is preferable because the blending ratios of the chlorinated isocyanuric acid and the effervescent agent are not relatively lowered and hence effective chlorine content and bubbling ability do not decrease.

Furthermore, in carrying out the invention, a lubricant such as magnesium stearate, calcium stearate, or talc may be blended, if necessary, in the case that the molded product is used for applications other than bathwater and pool-water.

The compression molding product of effervescent chlorinated isocyanuric acid of the present invention can be produced by mixing a chlorinated isocyanuric acid, an organic acid, a carbonate salt, and a sodium sulfate and pressing the mixture to form a molded product, in accordance with a conventional method.

The shape of the effervescent chlorinated isocyanuric acid molded product of the invention may be any shape of granule, briquette, tablet, and the like.

The application of the effervescent chlorinated isocyanuric acid molded product of the invention is not limited to sterilization of bathwater, pool-water, and the like, and the molded product is widely applicable to the purpose of preventing proliferation of microorganisms and algae in cooling water for cooling tower or the like, fire-fighting water, lakes and marshes, and so forth, offensive odor emission, etc.

EXAMPLES

The following will describe the invention in detail with reference to Examples and Comparative Example but the invention is not limited to these Examples.

The starting materials and methods for evaluation tests used in Examples and Comparative Example are as follows.

(Starting Materials)
Anhydrous sodium dichloroisocyanurate (manufactured by Shikoku Chemicals Corporation, effective chlorine content: 63.5%)
Adipic acid (manufactured by Wako Pure Chemical Industries, Ltd., reagent)
Sodium bicarbonate (manufactured by Wako Pure Chemicals Industries, Ltd., reagent)
Sodium carbonate (manufactured by Wako Pure Chemicals Industries, Ltd., reagent)
Anhydrous sodium sulfate (manufactured by SHIKOKU CORPORATION, those having a particle diameter of (A) from 45 μm to less than 150 μm, (B) from 150 μm to less than 355 μm, and (C) from 355 μm to less than 500 μm were prepared by sieving)

(Storage Stability Test (1))
Five tablets each having a weight of 5.5 g were placed in a 1 L plastic container and an opening for measuring decomposition gases was provided at its inner lid. The opening was tightly sealed with an adhesive tape and the container was stored in a constant-temperature and constant-humidity chamber set at 40° C. at a relative humidity of 75%. After the passage of 30 days and 60 days, concentrations of chlorine gas and chloramine gas generated in the plastic container were measured using a detector tube (manufactured by Gastec Corporation, Model No. 8).

It was judged that lower concentrations of these decomposition gases showed an excellent storage stability.

(Bubbling Test)

A tablet was put into a 2 L beaker in which 1 L of warm water (40° C.) was placed and the period of time from the start of bubbling of the tablet until the end of bubbling was measured and was determined as a bubbling time. In general, the larger the contents of the organic acid and the carbonate salt contained in the tablet are, the faster the tablet bubbles and the expansion and disintegration of the tablet proceed, so that the bubbling time is shortened.

(Storage Stability Test (2))

Five tablets each having a weight of 5.5 g were placed in a wrapping bug of polypropylene film (thickness of 70μ), which was tightly sealed by heat sealing. The wrapped one was stored in a constant-temperature and constant-humidity chamber set at 40° C. at a relative humidity of 75% to conduct heating and humidification for 60 days. Before and after the heating and humidification, the weight of the tablets was measured to calculate the amount of absorbed moisture (%) of the tablets after the heating and humidification. Moreover, before and after the heating and humidification, the bubbling time of the tablets was measured by conducting the bubbling test on the tablets. It was judged that smaller amount of absorbed moisture and shorter bubbling time showed an excellent storage stability.

Example 1

A blend was prepared by mixing 100 parts by weight of anhydrous sodium dichloroisocyanurate, 53 parts by weight of adipic acid and 44 parts by weight of fumaric acid as organic acids, 30 parts by weight of sodium bicarbonate and 40 parts by weight of sodium carbonate as carbonate salts, and 67 parts by weight of anhydrous sodium sulfate having a particle diameter of from 45 μm to less than 150 μm.

Then, 5.5 g of the above blend was placed in mortar and pestle having a diameter of 20 mm and a tablet was produced by pressurization at 1000 kg/cm². The resulting tablet was subjected to the evaluation tests and the test results were as shown in Table 1.

Additionally, 20 g of the above blend was placed in mortar and pestle having a diameter of 30 mm and, after pressurization at 1000 kg/cm², extrusion pressure necessary for taking the molded product out of the mortar and pestle was measured. The extrusion pressure was as shown in Table 1.

Example 2

A blend was prepared in the same manner as in Example 1 except that anhydrous sodium sulfate having a particle diameter of from 150 μm to less than 355 μm was used, and a tablet having a diameter of 20 mm was produced and subjected to the evaluation tests.

Additionally, the above blend was placed in mortar and pestle having a diameter of 30 mm and pressurized to measure extrusion pressure necessary for taking the molded product out of the mortar and pestle.

The test results were as shown in Table 1.

Comparative Example 1

A blend was prepared in the same manner as in Example 1 except that anhydrous sodium sulfate having a particle diameter of from 355 μm to less than 500 μm was used, and a tablet having a diameter of 20 mm was produced and subjected to the evaluation tests. Additionally, the above blend was placed in mortar and pestle having a diameter of 30 mm and pressurized to measure extrusion pressure necessary for taking the molded product out of the mortar and pestle.

The test results were as shown in Table 1.

Comparative Example 2

In mortar and pestle having a diameter of 20 mm was placed 5.5 g of a blend prepared by mixing 100 parts by weight of anhydrous sodium dichloroisocyanurate, 74 parts by weight of adipic acid and 61 parts by weight of fumaric acid as organic acids, 43 parts by weight of sodium bicarbonate and 56 parts by weight of sodium carbonate as carbonate salts, and the blend was pressurized at 1000 kg/cm² to produce a tablet.

The resulting tablet was subject to the evaluation tests and the test results obtained were as shown in Table 1.

TABLE 1

|  | Example | | Comparative Example | |
|---|---|---|---|---|
|  | 1 | 2 | 1 | 2 |
| Formulation (parts by weight) | | | | |
| Anhydrous sodium dichloroisocyanurate | 100 | 100 | 100 | 100 |
| Adipic acid | 53 | 53 | 53 | 74 |
| Fumaric acid | 44 | 44 | 44 | 61 |
| Sodium bicarbonate | 30 | 30 | 30 | 43 |
| Sodium carbonate | 40 | 40 | 40 | 56 |
| Anhydrous sodium sulfate (45 μm to less than 150 μm) | 67 | | | |
| Anhydrous sodium sulfate (150 μm to less than 355 μm) | | 67 | | |
| Anhydrous sodium sulfate (355 μm to less than 500 μm) | | | 67 | |
| Evaluation test | | | | |
| Chlorine gas (30 days after heating and humidification), ppm | 0 | 0 | 0 | 5 |
| Chlorine gas (60 days after heating and humidification), ppm | 0 | 0 | trace | 20 |
| Chloramine gas (30 days after heating and humidification), ppm | 250 | 250 | 500 | 600 |
| Chloramine gas (60 days after heating and humidification), ppm | 300 | 300 | 1000 | 1500 |
| Amount of moisture absorption, % | 1.61 | 1.62 | 1.62 | 1.61 |
| Bubbling time (before heating and humidification), sec. | 129 | 127 | 129 | 105 |
| Bubbling time (60 days after heating and humidification), sec. | 130 | 128 | 138 | 125 |
| Extrusion pressure, kg/cm² | 148 | 146 | 249 | |

According to the test results shown in Table 1, the chlorinated isocyanuric acid tablets containing anhydrous sodium sulfate of the invention exhibit suppressed generation of chlorine gas and chloramine gas after heating and humidification and hence are recognized to have an excellent storage stability as compared with the chlorinated isocyanuric acid tablet containing no anhydrous sodium sulfate of Comparative Example. Moreover, the use of anhydrous sodium sulfate having a particle diameter of 45 μm to less than 355 μm can further enhance storage stability.

Namely, in order to suppress the decomposition of the chlorinated isocyanuric acid, it is effective to use anhydrous sodium sulfate having a particle diameter of less than 355 μm.

Moreover, in the chlorinated isocyanuric acid tablets containing anhydrous sodium sulfate having a particle diameter of from 45 μm to less than 150 μm and having a particle diameter of from 150 μm to less than 355 μm of Examples 1 and 2, no difference in the bubbling time before and after the heating and humidification was observed. However, in the chlorinated isocyanuric acid tablets containing anhydrous sodium sulfate having a particle diameter of from 355 μm to less than 500 μm of Comparative Example 1 and the chlorinated isocyanuric acid tablets containing no anhydrous sodium sulfate of Comparative Example 2, the bubbling time after the heating and humidification increases.

The reason for these results seems to be that the decomposition of the carbonate salt is suppressed by the use of anhydrous sodium sulfate having a particle diameter of from 45 μm to less than 355 μm.

Furthermore, the chlorinated isocyanuric acid tablets containing anhydrous sodium sulfate having a particle diameter of from 45 μm to less than 150 μm and having a particle diameter of from 150 μm to less than 355 μm of Examples 1 and 2 were able to be taken out of the mortar and pestle with extrusion pressure of about 150 kg/cm$^2$.

However, in the case of the chlorinated isocyanuric acid tablet containing anhydrous sodium sulfate having a particle diameter of from 355 μm to less than 500 μm of Comparative Example 1, the extrusion pressure of about 250 kg/cm$^2$ was necessary at the time when the molded product was taken out of the mortar and pestle.

Namely, the chlorinated isocyanuric acid molded products containing anhydrous sodium sulfate having a particle diameter of less than 355 μm show a small frictional drag with the mortar and pestle, so that abrasion of the mortar and pestle can be reduced as compared with the case of anhydrous sodium sulfate having a particle diameter of from 355 μm to less than 500 μm.

While the invention has been described in detail and with reference to specific embodiments thereof, it will be apparent to one skilled in the art that various changes and modifications can be made therein without departing from the scope thereof.

This application is based on Japanese patent applications No. 2003-287668 filed on Aug. 6, 2003, the entire contents thereof being hereby incorporated by reference.

What is claimed is:

1. A compression molded product of effervescent chlorinated isocyanuric acid, comprising:
    (a) 100 parts by weight of sodium dichloroisocyanurate,
    (b) organic acid,
    (c) carbonate salt, and
    (d) 40-80 parts by weight of sodium sulfate, wherein said sodium sulfate has a particle diameter of from 45 μm to less than 355 μm and is not subjected to a surface treatment with a lubricant.

2. The compression molded product according to claim 1, wherein
    the organic acid is contained in an amount of from 50 to 200 parts by weight, and
    the carbonate salt is contained in an amount of from 50 to 200 parts by weight.

3. A process for producing a compression molded product of effervescent chlorinated isocyanuric acid, which comprises molding under compression a composition comprising:
    (a) 100 parts by weight of sodium dichloroisocyanurate,
    (b) organic acid,
    (c) carbonate salt, and
    (d) 40-80 parts by weight of sodium sulfate, wherein
    said sodium sulfate has a particle diameter of from 45 μm to less than 355 μm and is not subjected to a surface treatment with a lubricant.

4. The process according to claim 3, wherein the molding under compression is achieved by using a mortar and pestle.

* * * * *